(12) United States Patent
MacFarland

(10) Patent No.: US 10,634,656 B2
(45) Date of Patent: Apr. 28, 2020

(54) STORAGE STABLE STANDARDS FOR AQUEOUS CHLORINE ANALYSIS

(71) Applicant: Hach Company, Loveland, CO (US)

(72) Inventor: Darren MacFarland, Windsor, CO (US)

(73) Assignee: HACH COMPANY, Loveland, CO (US)

(*) Notice: Subject to any disclaimer, the term of this patent is extended or adjusted under 35 U.S.C. 154(b) by 629 days.

(21) Appl. No.: 15/337,296

(22) Filed: Oct. 28, 2016

(65) Prior Publication Data

US 2017/0122922 A1 May 4, 2017

Related U.S. Application Data

(60) Provisional application No. 62/248,560, filed on Oct. 30, 2015.

(51) Int. Cl.

| | |
|---|---|
| *G01N 33/18* | (2006.01) |
| *G01N 1/28* | (2006.01) |
| *B01L 3/00* | (2006.01) |
| *G01N 31/22* | (2006.01) |
| *G01N 27/416* | (2006.01) |

(52) U.S. Cl.
CPC ............ *G01N 33/182* (2013.01); *B01L 3/523* (2013.01); *G01N 1/28* (2013.01); *G01N 31/22* (2013.01); *G01N 33/18* (2013.01); *B01L 2200/14* (2013.01); *B01L 2200/16* (2013.01); *B01L 2300/0835* (2013.01); *G01N 27/4168* (2013.01); *G01N 2001/2893* (2013.01)

(58) Field of Classification Search
CPC ...... G01N 33/182; G01N 31/22; G01N 21/77; G01N 27/4168; G01N 31/00; G01N 33/18; C02F 2209/29; C02F 1/76; B01L 2200/16; B01L 2300/0835
See application file for complete search history.

(56) References Cited

U.S. PATENT DOCUMENTS

| | | | | |
|---|---|---|---|---|
| 3,338,837 A | * | 8/1967 | Hodes ...................... | C11D 1/00 424/606 |
| 3,893,954 A | * | 7/1975 | Tivin ........................ | C11D 3/30 252/188.1 |
| 2009/0320570 A1 | * | 12/2009 | Wiese .................... | G01N 31/16 73/61.43 |

OTHER PUBLICATIONS

Choi, Junghoon et al. "Mechanistic studies of N-nitrosodimethylamine (NDMA) formation in chlorinated drinking water", 2002, J. Environ. Monit., 4, p. 249-252. (Year: 2002).*
Ammonia-Dimethylchloramine System—Kinetic Approach in an Aqueous Medium and Camparison With the Mechanism Involving Liquid Ammonia, Stephan, J, et al., International Journal of Chemical Kinetics, pp. 340-351, Dec. 10, 2007.

* cited by examiner

*Primary Examiner* — Lyle Alexander
*Assistant Examiner* — Bryan Kilpatrick
(74) *Attorney, Agent, or Firm* — Ference & Associates LLC

(57) ABSTRACT

A standard for testing measurement systems for aqueous chlorine species analysis includes an openable storage vessel and an aqueous composition including a compound having the formula $R_1R_2NCl$ where $R_1$ and $R_2$ are independently methyl, ethyl or propyl, wherein the aqueous composition is storage stable within the openable storage vessel.

20 Claims, 2 Drawing Sheets

STORAGE STABLE STANDARDS FOR AQUEOUS CHLORINE ANALYSIS

CROSS REFERENCE TO RELATED APPLICATION

This application claims priority to U.S. Provisional Patent Application Ser. No. 62/248,560, filed on Oct. 30, 2015, and entitled "STORAGE STABLE STANDARDS FOR AQUEOUS CHLORINE ANALYSIS," the contents of which are incorporated by reference herein.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Chlorination of water supplies is the most prevalent form of water disinfection. Chlorination introduces oxidizing agents that kill microorganisms present in the water. The two primary water disinfectants used in the United States are free chlorine (as hypochlorite) and chloramines (compounds of chlorine and ammonia).

Measurement of chlorine levels in water is used to determine the amount of chlorination needed for a water supply. Accurate determination of chlorine levels in water is very important to ensure safety. Overestimation of chlorine levels can lead to dangerously inadequate disinfection, while underestimation of chlorine levels and associated overchlorination can lead to unwanted by products, as well as unpleasant tastes and odors.

There are several analytical methods for the determination of chlorine in water. The most widely used analytical method is the DPD (N, N-diethyl-p-phenylenediamine) method. Absorbance (for example, at 515 nm) may, for example, be spectrophotometrically measured to determine free chlorine, chloramines, and/or total chlorine concentration.

Analytical instruments for chlorine species analysis, such as spectrometers used in, for example, the DPD chlorine method, may be tested and/or calibrated using standards. A standard is a composition that contains a known concentration of a chemical, species or analyte of interest. Standards are used, for example, to determine precision and accuracy of a test method, to determine proper functioning of test equipment, and skills and techniques of analysts. Unfortunately, standards for measuring chlorine species (including free chlorine and/or total chlorine) are limited because of an instability/relatively quick decomposition.

BRIEF SUMMARY

In one aspect, a standard for testing measurement systems for aqueous chlorine species analysis includes an openable storage vessel and an aqueous composition including a compound having the formula $R_1R_2NCl$ where $R_1$ and $R_2$ are independently methyl, ethyl or propyl, wherein the aqueous composition is storage stable within the openable storage vessel. $R_1$ and $R_2$ may, for example, be methyl groups.

In a number of embodiments, the chlorine content as measured $Cl_2$ of the aqueous composition within the storage vessel changes by less than 20% over a period of 3 months at 30° C. The chlorine content as measured $Cl_2$ may, for example, range from approximately 50 ppb to approximately 5 ppm by weight.

The storage vessel may, for example, be airtight. In a number of embodiments, the storage vessel is a glass ampoule.

The aqueous composition may, for example, be buffered, and its pH may, for example, be between approximately 7 and 12. In a number of embodiments, the buffer includes at least one of citrate, carbonate and phosphate.

In another aspect, a method to produce an aqueous standard for use in testing measurement systems for chlorine species analysis includes forming an aqueous composition including a compound having the formula $R_1R_2NCl$ where $R_1$ and $R_2$ are independently methyl, ethyl, and propyl; and storing the aqueous composition within an openable storage vessel, wherein the aqueous composition is storage stable. As discussed above, in a number of embodiments, $R_1$ and $R_2$ are methyl groups.

The aqueous composition may, for example, be formed by mixing a free chlorine solution in a buffer at a pH of at least 7 with a reactant having the formula $R_1R_2NH$ at a temperature between 0 and 40° C. The molar ratio of the reactant to the free chlorine may, for example, be in the range of approximately 2 to 1000.

In a further aspect, a kit used for testing measurement systems for total chorine analysis includes a container having therein at least one openable storage vessel. The openable storage vessel contains an aqueous composition including a compound having the formula $R_1R_2NCl$ wherein $R_1$ and $R_2$ are independently methyl, ethyl, and propyl, wherein the aqueous standard is storage stable within the openable storage vessel. In a number of embodiments, $R_1$ and $R_2$ are methyl groups. In a number of embodiments, the chlorine content, as measured $Cl_2$, of the aqueous composition within the storage vessel changes preferably by less than 20% over a period of 3 months at 30° C. The chlorine content, as measured $Cl_2$, may, for example, range from approximately 50 ppb to approximately 5 ppm by weight. In a number of embodiments, the container has a plurality of openable storage vessels therein. Each of the plurality of openable storage vessels contains the aqueous composition including a compound having the formula $R_1R_2NCl$, wherein the aqueous standard is storage stable within the openable storage vessels.

The present systems, methods and compositions, along with the attributes and attendant advantages thereof, will best be appreciated and understood in view of the following detailed description taken in conjunction with the accompanying drawings.

DETAILED DESCRIPTION

Figure 1:
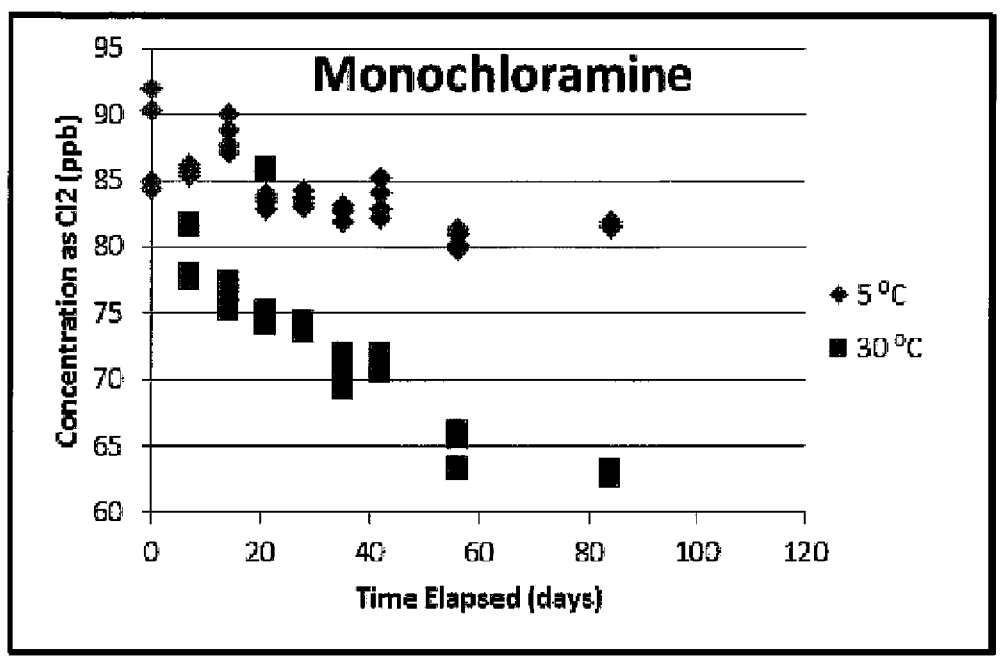
FIG. 1 illustrates shelf life stability of a monochloramine solution over 3 months, wherein stability is measured as the concentration of chlorine (as $Cl_2$).

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a compound" includes a plurality of such compounds and equivalents thereof known to those skilled in the art, and so forth, and reference to "the compound" is a reference to one or more such compounds and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

Chlorination of public water supplies has been practiced for almost 100 years in the United States. Chlorine usually is added to water as the gaseous form or as sodium or calcium hypochlorite. The two chemical species formed by chlorine hydrolysis, hypochlorous acid (HOCl) and hypochlorite ion (OCl$^-$), are commonly referred to as "free available" chlorine.

Ammonia, commonly present in natural waters, will react with hypochlorous acid or hypochlorite ion to form monochloramine, dichloramine and trichloramine, depending on several factors such as pH and temperature. In solution, mono-, di-, and tri-chloramine coexist in equilibrium. pH is the major factor controlling the proportion of each species with trichloramine being favored at acidic pH, dichloramine being favored near neutral pH, and monochloramine being favored at basic pH. Added chloramines are also used as a disinfectant for drinking water (chloramination process).

As described above, a common chlorine test method is the DPD (N, N-diethyl-p-phenylenediamine) colorimetric test. It can determine both free chlorine and total chlorine concentration. Total chlorine is the total amount of chlorine in the water including free chlorine and combined chlorine (including chlorine that has reacted with nitrogen compounds). In the absence of iodide ion, free chlorine reacts quickly with DPD indicator to produce a red color, whereas chloramines react more slowly. If a small amount of iodide ion is added, chloramines also react quickly to produce color, yielding total chlorine concentration. Chloramine concentration can then be determined by difference. Absorbance (for example, at 515 nm) may be spectrophotometrically measured and compared to a series of standards, using, for example, a graph or a regression analysis calculation to determine free chlorine, chloramine, and/or total chlorine concentration.

"Standard" DPD colorimetric methods include the US EPA approved Standard Methods 4500-C1 G and International Organization for Standardization (ISO) Method 7393/2. The test range of the two methods are 0.01-4 mg/L and 0.03-5 mg/L as Cl$_2$, respectively.

Analytical test equipment, for example spectrometers, must be calibrated periodically to ensure accuracy and precision of results. In many instances the calibration procedure is accomplished using standard compositions/solutions. A standard composition or solution is a composition that includes a known concentration of a particular chemical/species. Standard compositions are, for example, used to test and calibrate spectrometers used in chlorine testing.

Calibration procedures for the DPD tests generally include the use of free-chlorine solutions. Standard free chlorine solutions may be difficult to prepare because all glassware must be chlorine-demand free and the water must be organic-free deionized water. In addition, in the presence of light, contaminates, or catalysts; free chlorine will decompose to chlorine gas, hydrochloric acid, etc. For this reason, chlorine standards solutions are normally prepared in sealed glass ampoules. They typically must be used immediately after breaking the seal.

Chloramines have not been used to calibrate chlorine testing equipment because the chlorinated ammonia derivatives are subject to multiple equilibria (as discussed above), leading to multiple forms and decomposition pathways. Chloramines are inherently unstable. The auto-decomposition of monochloramine, for example, can be simplified to the following chemical reaction:

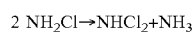

$$2\ NH_2Cl \rightarrow NHCl_2 + NH_3$$

Chloramines will also react with contaminates like organics and reductants present in water. Thus, over time, concentration of chloramines in solution will decrease. For these reasons, the shelf life of chloramine solutions have been too short to be useful as standard solutions.

Unlike chloramines formed from ammonia, the reaction of chlorine with secondary amines, (those with the general structure of R$_1$R$_2$NH) leads only to the corresponding dialkylchloramine products, R$_1$R$_2$NCl. Multiple equilibria that plague ammonia-based chloramines described above are eliminated. Moreover, it has been found that water soluble dialkylchloramines (for example, those with the general structure of R$_1$R$_2$NCl where R$_1$ and R$_2$ are independently methyl, ethyl, or propyl) are more stable than the ammonia-based chloramines.

Figure 2:
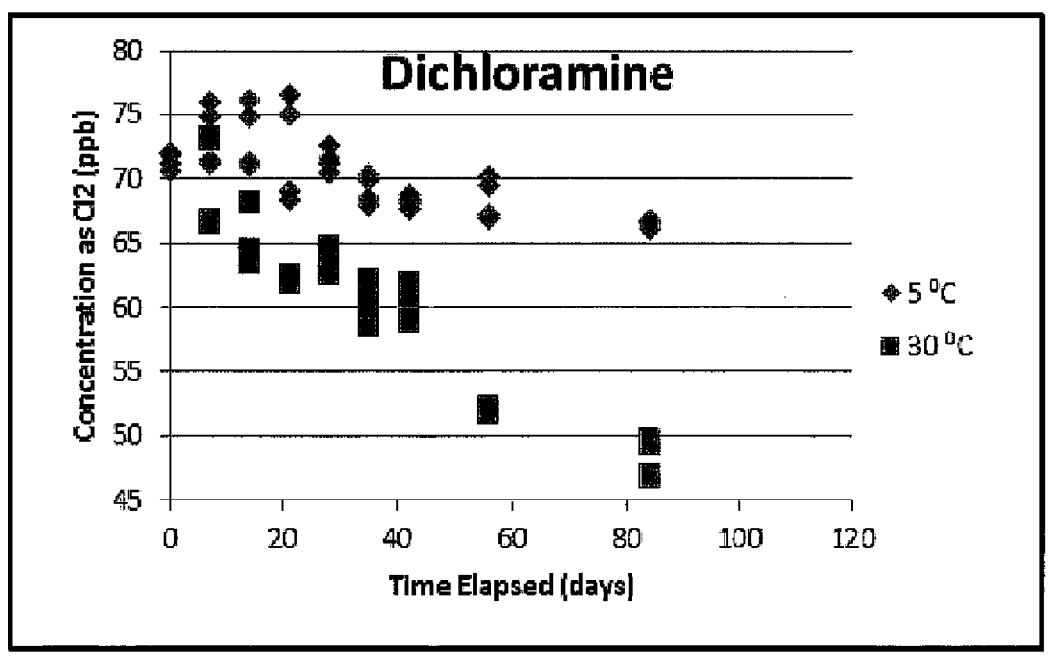
FIG. 2 illustrates shelf life stability of a dichloramine solution over 3 months, wherein stability is measured as the concentration of chlorine (as $Cl_2$).
Figure 3:
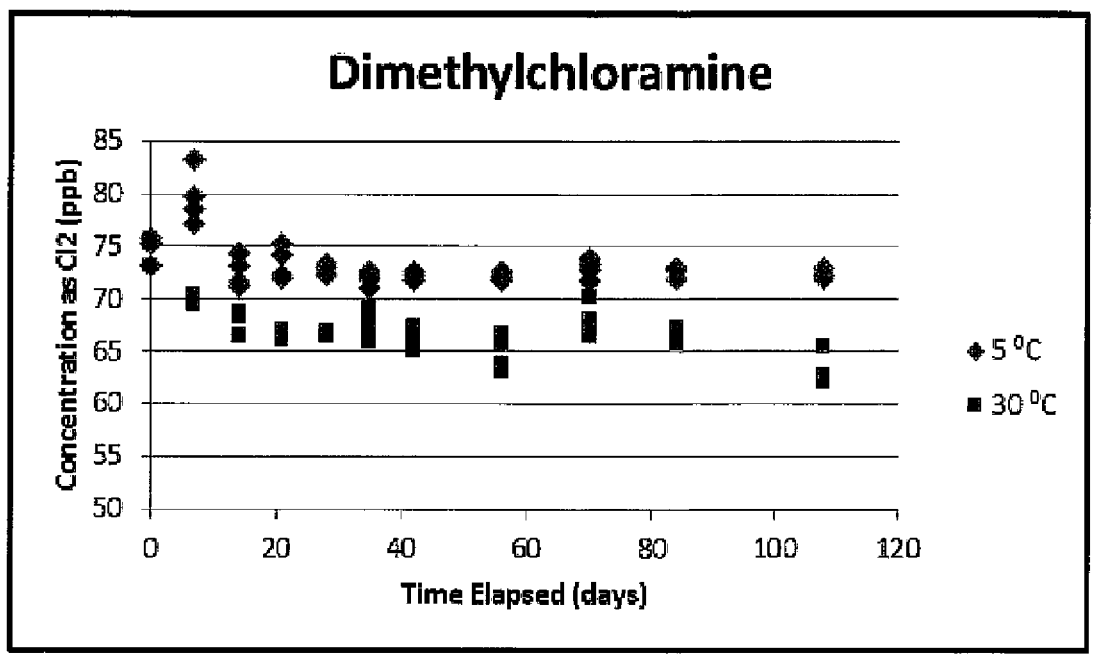
FIG. 3 illustrates shelf life stability of a dimethylchloramine solution over 4 months, wherein stability is measured as the concentration of chlorine (as $Cl_2$).

FIGS. 1-3 show the result of aging tests of various chloramines conducted in airtight containers at temperatures of 5 and 30° C. FIGS. 1 and 2 depict decomposition of monochloramine and dichloramine, respectively, over time at 5 and 30° C. Decomposition rates are greater as temperature increases. At 30° C., monochloramine concentration (as ppb $Cl_2$) decreased from about 80 to 63 ppb over 80 days (21%), while dichloramine concentration (as ppb $Cl_2$) decreased from about 70 to 47 ppb over 80 days (33%).

As shown in FIG. 3, dimethylchloramine is substantially more stable than either monochloramine or dichloramine. At both 5 and 30° C., dimethylchloramine concentration was stable over at least 120 days in an airtight container. Standard compositions used for the DPD test can be prepared with chlorine concentrations (as $Cl_2$) between, for example, about 20 and 500 ppb, corresponding to the test ranges of the two standard DPD colorimetric methods described above. To facilitate use as a standard, it is desirable that standards hereof be storage stable. In that regard, in the standards hereof measured chlorine concentration changes by no more than 20%, 15%, or 13% after three months or 90 days storage at 30° C. In the case of an 80 ppb standard solution, chlorine concentration (as $Cl_2$) thus does not change by more than 16, 12 or 10 ppb as a result of three months or 90 days storage at 30° C. Representative studies indicate that the measured chlorine concentration does not change by more than 13% after four months (120 days) or longer for standards hereof stored at 30° C. Improved stability may be achieved at lower storage temperature. In that regard, in the standards hereof, measured chlorine concentration changed by no more than 10% after four months or 120 days storage at 5° C.

As can be seen in FIGS. 1 and 2, standard compositions of monochloramine and dichloramine do not meet the stability criteria set forth above. Likewise, a standard solution of dimethylchloramine (see FIG. 3) does meet the stability criteria.

In a number of representative examples, water soluble dialkylchloramines, as described above, were prepared under the following procedure. An organic-free and oxidant-free water, buffered solution with pH between 7-12 was used. In a number of embodiments, the pH was between 8 and 10. A phosphate-citrate buffer was used in a number of embodiments. A suitable temperature range is, for example, between 0 and 40° C. Free chlorine was added to obtain the desired final concentration (for example, between 20 and 500 ppb as $Cl_2$). The desired dialkylamine was then added such that the final molar ratio of dialkylamine to free chlorine was between 2 and 1000. The resultant standard solution was then stored in suitable contaminate-free, airtight containers, such as glass ampoules.

In a number of studies hereof, a standard solution of dimethylchloramine was prepared. Dimethylamine was mixed with a free chlorine solution as described above at room temperature (approximately 25° C.) in a phosphate-citrate buffer with pH approximately 8.5. The free chlorine was limiting, and the dimethylamine was present in a large excess. Final concentration of chlorine (as $Cl_2$) in a number of studied embodiments was 0.3 mg/L or 300 ppb. The dimethylchloramine composition was stored in an airtight storage vessel or container such as a glass ampoule.

In a number of representative studies, standard compositions of dimethylchloramine were used in an HACH® CM130 spectrometer (Hach Company, Loveland, Colo. US). First, a 20 ml ampoule of dimethylchloramine solution (approximately 300 ppb $Cl_2$) was mixed with clean, organic-free water (55 mL) to make a solution at 80 ppb. It is also preferable that the water be reductant-free and oxidant free. The mixed 80 ppb solution was then poured manually into the spectrometer to wash the measurement chamber a few times and to provide a sample to be measured.

Figure 4:
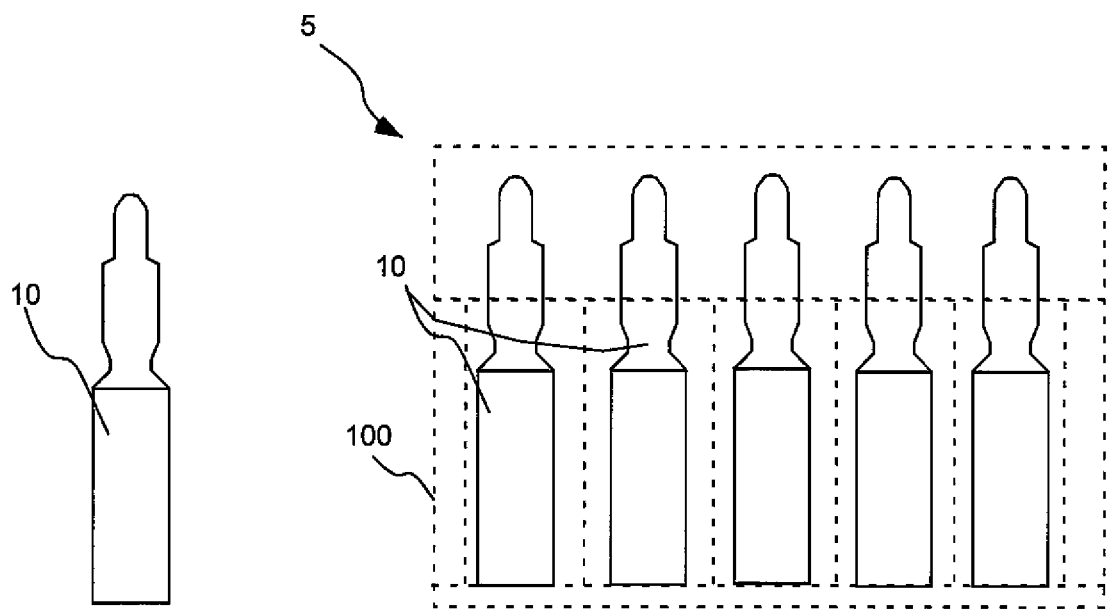
FIG. 4 illustrates schematically a kit including a plurality of storage vessels enclosing a standard composition hereof within a container such as a box.

As illustrated in FIG. 4, kits 5 of standard compositions hereof may, for example, be prepared by packaging one or more sealed, airtight storage vessels 10 (for example, glass ampoules) in an appropriate container 100 (for example, a partitioned box, suitable for storage and shipping).

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A standard for testing measurement systems for aqueous chlorine species analysis, comprising an openable storage vessel and an aqueous composition comprising a compound having the formula $R_1R_2NCl$, wherein $R_1$ is selected from the group consisting of: methyl, ethyl or propyl and wherein $R_2$ is selected from the group consisting of: methyl, ethyl or propyl, wherein the aqueous composition comprises dimethylchloramine, wherein the aqueous composition is storage stable within the openable storage vessel.

2. The standard of claim 1 wherein $R_1$ and $R_2$ are methyl groups.

3. The standard of claim 1 wherein the chlorine content as measured $Cl_2$ of the aqueous composition within the storage vessel changes by less than 20% over a period of 3 months at 30° C.

4. The standard of claim 1 wherein the chlorine content as measured $Cl_2$ ranges from approximately 50 ppb to approximately 5 ppm by weight.

5. The standard of claim 1 wherein the storage vessel is airtight.

6. The standard of claim 1 wherein the storage vessel is a glass ampoule.

7. The standard of claim 1 wherein the aqueous composition is buffered and its pH is between approximately 7 and 12.

8. The standard of claim 7 wherein the buffer is selected from the group consisting of citrate, carbonate and phosphate.

9. A method to produce an aqueous standard for use in testing measurement systems for chlorine species analysis, comprising:
    forming an aqueous composition comprising a compound having the formula $R_1R_2NCl$, wherein $R_1$ is selected from the group consisting of: methyl, ethyl or propyl and wherein $R_2$ is selected from the group consisting of: methyl, ethyl, and propyl, wherein the aqueous composition comprises dimethylchloramine; and
    storing the aqueous composition within an openable storage vessel, wherein the aqueous composition is storage stable.

10. The method of claim 9 wherein $R_1$ and $R_2$ are methyl groups.

11. The method of claim 9 wherein the chlorine content as measured $Cl_2$ of the aqueous composition within the storage vessel changes preferably by less than 20% over a period of 3 months at 30° C.

12. The method of claim 9 wherein the aqueous composition is buffered and its pH is between approximately 7 and 12.

13. The method of claim 9 wherein the chlorine content as measured $Cl_2$ ranges from approximately 50 ppb to approximately 5 ppm by weight.

14. The method of claim 9 wherein the aqueous composition is formed by mixing a free chlorine solution in a buffer at a pH of at least 7 with a reactant having the formula $R_1R_2NH$ at a temperature between 0 and 40° C.

15. The method of claim 14 wherein a range of the molar ratio of the reactant to the free chlorine is approximately 2:1000.

16. A kit used for testing measurement systems for total chorine analysis, comprising:
    a container having therein at least one openable storage vessel,
    the openable storage vessel containing an aqueous composition comprising a compound having the formula $R_1R_2NCl$, wherein $R_1$ is selected from the group consisting of: methyl, ethyl or propyl and wherein $R_2$ is selected from the group consisting of: methyl, ethyl, and propyl, wherein the aqueous composition comprises dimethylchloramine, wherein the aqueous standard is storage stable within the openable storage vessel.

17. The kit of claim 16 wherein $R_1$ and $R_2$ are methyl groups.

18. The kit of claim 16 wherein the chlorine content as measured $Cl_2$ of the aqueous composition within the storage vessel changes preferably by less than 20% over a period of 3 months at 30° C.

19. The kit of claim 16 wherein the chlorine content as measured $Cl_2$ ranges from approximately 50 ppb to approximately 5 ppm by weight.

20. The kit of claim 16 wherein the container has a plurality of openable storage vessels therein, each of the plurality of openable storage vessels containing the aqueous composition comprising a compound having the formula $R_1R_2NCl$, wherein the aqueous standard is storage stable within the openable storage vessels.

* * * * *